United States Patent [19]

Shaya et al.

[11] Patent Number: 4,664,116
[45] Date of Patent: May 12, 1987

[54] PACE PULSE IDENTIFICATION APPARATUS

[75] Inventors: Mousa N. Shaya, Newtonville; Barry L. Wyshogrod, Brookline, both of Mass.

[73] Assignee: Hewlett-Packard Company, Palo Alto, Calif.

[21] Appl. No.: 601,525

[22] Filed: Apr. 18, 1984

[51] Int. Cl.[4] .............................................. A61B 9/04
[52] U.S. Cl. .............................. 128/419 PT; 128/697
[58] Field of Search .............................. 128/696–697, 128/419 PT, 419 PG, 708, 901–902

[56] References Cited

U.S. PATENT DOCUMENTS

| | | | |
|---|---|---|---|
| 3,520,295 | 7/1970 | Kelly | 128/708 |
| 3,605,727 | 9/1971 | Zenevich et al. | 128/704 |
| 3,780,727 | 12/1973 | King | 128/697 |
| 3,923,041 | 12/1975 | Stasz et al. | 128/697 |
| 3,986,496 | 10/1976 | Brastad | 128/697 |
| 4,240,442 | 12/1980 | Andresen et al. | 128/708 |
| 4,393,874 | 7/1983 | Nappholz et al. | 128/697 |

OTHER PUBLICATIONS

Webster, "Reducing Motion Artifacts and Interference in Biopotential Recording", *IEEE Trans. Biomed. Eng.*, vol. BME-31, No. 12, Dec. 1984, pp. 823–826.

*Primary Examiner*—William E. Kamm
*Attorney, Agent, or Firm*—Donald N. Timbie

[57] ABSTRACT

A pace pulse identification apparatus in which low frequency signals are rejected by a filter and the pace pulses and high frequency noise are applied to one input of a comparator. A threshold wave having an amplitude that is not significantly affected by pace pulses or spikes of noise is provided that has a minimum value when steady high frequency noise is absent and a value equal to the sum of the minimum value and a value that varies with the amplitude of high frequency noise when high frequency noise is present and which is applied to the other input of the comparator. The state of the comparator is changed when a pace pulse is present at the output of the filter because its amplitude exceeds that of the threshold wave.

10 Claims, 4 Drawing Figures

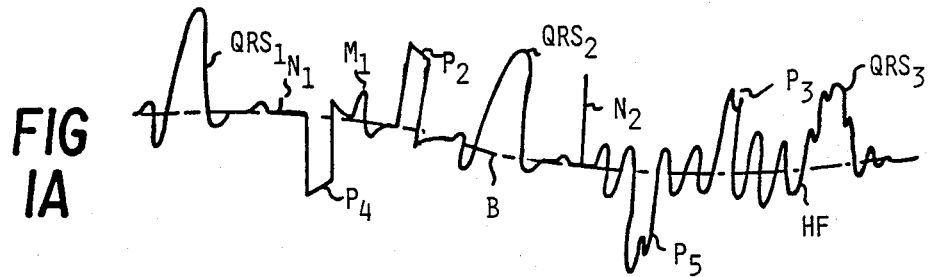
FIG IA
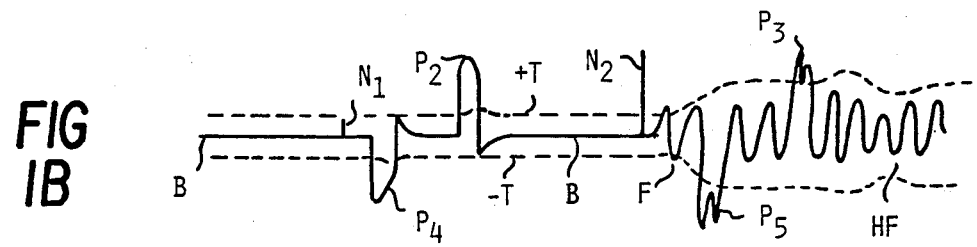
FIG IB
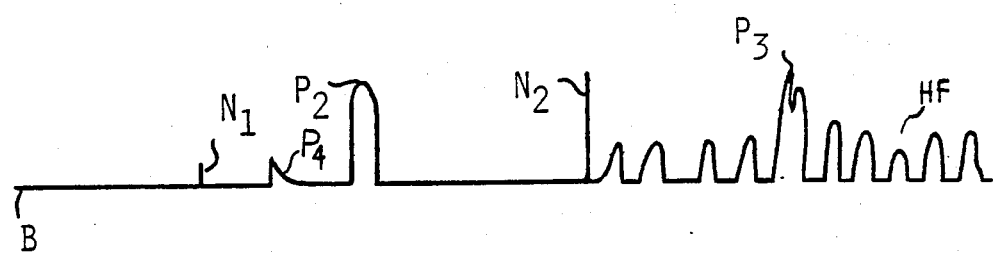
FIG IC

PACE PULSE IDENTIFICATION APPARATUS

BACKGROUND OF THE INVENTION

In monitoring the heart action of a patient having a pacemaker, it is essential to positively identify the pacemaker pulses contained in the signals detected via body electrodes if the software programs used for analysis are to function properly. Falsely identifying other signal components as pace pulses is as undesirable as failing to identify the true pace pulses. Although the pace pulses generally have an amplitude that is greater than steady high frequency noise, identification on the basis of amplitude alone is not feasible because the amplitudes of motion and muscle artifacts and QRS waves are often as great or greater than the amplitude of the pace pulses. Identification of pace pulses on the basis of amplitude is further complicated by the fact that the baseline often drifts at a low frequency and the fact that the absolute amplitudes of the signals vary widely. Identification of a pace pulse on the basis of width holds little promise because the widths of the pulses supplied by different makes of pacemakers vary from tens of microseconds to 2.5 milliseconds. Identification of the pace pulses must be sensitive to both positive-going and negative-going pace pulses. For these reasons, prior art apparatus has not identified the pace pulses in a satisfactory manner.

BRIEF SUMMARY OF THE INVENTION

In accordance with this invention, the signals detected via the body electrodes are passed through a high pass filter to one input of a comparator. The filter suppresses baseline wander, the ECG waves and the artifacts due to movement and muscle action, so that only pace pulses, noise spikes and high frequency noise reach the comparator. The output of the filter is also applied to means for deriving a threshold wave that is applied to the other input of the comparator. The means for deriving the threshold wave operates to suppress the effects of pace pulses on its amplitude and to cause it to have a minimum amplitude when steady high frequency noise is absent and an amplitude equal to the sum of the minimum amplitude and a value that varies with the amplitude of the peaks of steady high frequency noise when such noise is present. Under these conditions, the amplitude of the pace pulses will exceed that of the threshold wave so as to cause the comparator to change state and thus indicate that a pace pulse is present. Because the threshold wave has an amplitude that is at least as great as the peaks of steady high frequency noise, this noise does not cause false identifications.

Derivation of the threshold wave may be accomplished by a number of circuits, but in the embodiment shown, the circuit includes means for rectifying the signals passed by the high pass filter, means for deriving an average value thereof which has a time constant such that the average value is relatively unaffected by pace pulses and noise spikes, means for providing sufficient gain for the average value to be greater than the peaks of steady high frequency noise, and means for adding a fixed increment to the average value so as to provide the minimum value.

If it is desired to indicate the presence of a pace pulse regardless of polarity, the output of the high pass filter is applied to one input of each of two comparators, and opposite polarities of the threshold wave are respectively applied to the other input so that one comparator will change state in response to a positive pace pulse and the other comparator will change state in response to a negative pace pulse.

BRIEF DESCRIPTION OF THE DRAWINGS

FIG. 1A illustrates the type of signals supplied to a pace pulse identifier from electrodes attached to a patient;

FIG. 1B illustrates the signals at the output of the high pass filter employed and the relationship of the positive and negative threshold thereto; and FIG. 1C illustrates the portions of the signal at the output of the rectifier that lie on the positive side of the AC axis.

DETAILED DESCRIPTION OF THE INVENTION

Figure 1:
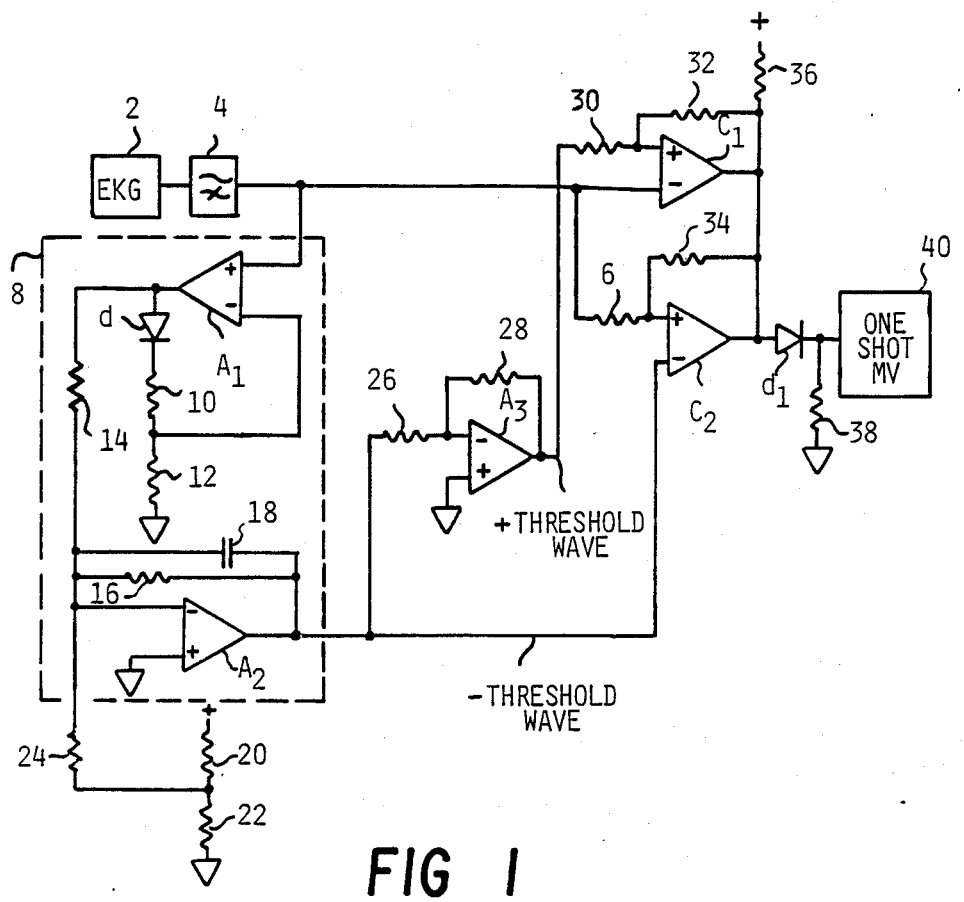
FIG. 1 is a schematic diagram illustrating a preferred embodiment of this invention.

In the embodiment of FIG. 1, an EKG machine 2 provides signals detected via the body electrodes. As illustrated in FIG. 1A, the signals vary about a drifting baseline B and include a muscle and motion artifact M, three QRS complexes $QRS_1$, $QRS_2$ and $QRS_3$ that are derived from different heart contractions, positive pace pulses $P_2$ and $P_3$ that respectively initiate the immediately following contractions represented by $QRS_2$ and $QRS_3$, noise spikes $N_1$ and $N_2$ and steady high frequency noise HF that may be caused by other electrical equipment. Pace pulses detected via the body electrodes may be of either polarity, so $P_4$ and $P_5$ are included in addition to $P_2$ and $P_3$ for completeness and explanatory purposes.

The signals of FIG. 1A provided by the EKG machine 2 are coupled to the input of a high pass filter 4 having a low frequency cut-off that is above the highest frequency of significance contained by the QRS complexes, the muscle and motion artifact M and the baseline drift so that the output of the high pass filter 4 is free from these components as illustrated by FIG. 1B. The output of the high pass filter 4 is applied to the negative input of a comparator $C_1$ and via a resistor 6 to the positive input of a comparator $C_2$. The output of the high pass filter 4 is also applied to means 8 for deriving the threshold wave previously referred to.

In this particular embodiment, the means 8 is comprised of a rectifying operational amplifier $A_1$ having its non-inverting input connected to the output of the filter 4, its output coupled to ground via a diode d, a resistor 10 and a resistor 12 that are connected in series in the order named, and its inverting input connected to the junction of the resistors 10 and 12. For reasons to be set forth below, the values of the resistors 10 and 12 are such as to provide a gain of a little more than 3.14 so that the signal at the output of the amplifier $A_1$ appears as indicated in FIG. 1C.

The output of the amplifier $A_1$ is connected via a resistor 14 to the inverting input of an operational amplifier $A_2$ having its non-inverting input connected to ground and its output connected to its inverting input via a parallel combination of a resistor 16 and a capacitor 18 so that the amplifier $A_2$ operates as an inverting integrator of unity gain. A minimum value for the threshold wave is provided as follows. Resistors 20 and 22 are connected in series between a point of positive DC voltage and ground, and a resistor 24 having the same value as the resistors 14 and 16 is connected between the junction of the resistors 20, 22 and the inverting input of the amplifier $A_2$.

Although the output of the amplifier $A_2$ is derived from the positive signals of FIG. 1C, it is, because of the inversion of $A_2$, a negative threshold wave having an amplitude relationship to the signals at the output of the filter 4 as indicated by the dashed wave $-T$ of FIG. 1B. The time constant provided by the resistor 16 and the capacitor 18 is such that the contribution of the pace pulses $P_2$ and $P_4$ and of the noise spikes $N_1$ and $N_2$ to the output of the integrating amplifier $A_2$ is suppressed, thus making the output have a minimum value equal to the DC voltage derived from the voltage divider 20, 22 when steady high frequency noise HF is absent. When, however, high frequency noise is present, as in the right half of FIG. 1B, the output of the itegrating amplifier $A_2$ becomes more negative by a voltage value that varies with the amplitude of the high frequency noise HF. Preferably, it is at least equal to and even slightly greater than the envelope of the positive half-cycles of the high frequency noise HF. Because of the time constant involved, the threshold wave does not reach its maximum value until several cycles of HF have occurred. This means that the comparator will change state so as to falsely identify a cycle such as F of FIG. 1B as a pace pulse; but this occurs only when the electrical equipment causing the high frequency noise HF is turned on or its state of operation is changed. Such infrequent false identification can be taken into account by the algorithm used to process the signals.

In this particular embodiment of the invention, the increase in negative voltage in response to HF is derived in the following way. It is reasonable to assume that the steady state high frequency noise at the output of the high pass filter 4 is sinusoidal. If the rectifying amplifier $A_1$ had unity gain, the average value of the half-sinusoids derived by the integrating amplifier $A_2$ would equal the amplitude of HF divided by $\pi$. Therefore, if a gain of $\pi$ is provided by the rectifying amplifier $A_1$, the average value derived by the integrating amplifier $A_2$ will be equal to the peak amplitude of the high frequency noise HF. Although not necessary, it is preferable that the gain of the rectifying amplifier $A_1$ be slightly greater than $\pi$, e.g., 3.6, in order to provide an extra margin of noise rejection, as may be required if HF is not sinusoidal. The output of the integrating amplifier $A_2$, at which $-T$ appears, is connected to the negative input of $C_2$.

A positive threshold wave which is ilustrated by a dashed line $+T$ in FIG. 1B is derived from the negative threshold wave by inverting it in any suitable manner as with an operational amplifier $A_3$. The negative threshold wave is applied via a resistor 26 to the inverting input of the amplifier $A_3$. A resistor 28 which is equal in value to the resistor 26 is connected between the output of $A_3$ and its inverting input, and the non-inverting input of $A_3$ is connected to ground. The positive threshold wave $+T$ produced at the output of $A_3$ is applied to the non-inverting input of the comparator $C_1$ via a resistor 30, and a resistor 32 is connected between the noninverting input of $C_1$ and its output. A resistor 34 is connected between the non-inverting input of $C_2$ and its output, and the outputs of $C_1$ and $C_2$ are connected via a resistor 36 to a point of positive potential. Resistors 6, 30, 32 and 34 provide hysterysis.

The time constant of the integrating amplifier $A_2$ determined by the resistor 16 and the capacitor 18 can have different values, but a value equal to at least ten times the width of wide pace pulses has been found to work well. If the time constant is too short, pace pulses and noise spikes will increase the values of the threshold waves so as to decrease the sensitivity. Sensitivity is also decreased as the minimum value of the threshold wave is increased. Obviously, if the time constant is so short that the pace pulses appear with full ampltude in the threshold waves, the states of the comparators $C_1$ and $C_2$ would not change and the circuit would be inoperative.

Whereas it is preferable for the variable increment of voltage that is added to the minimum value of the threshold wave to at least equal the amplitude of the steady high frequency noise, a somewhat lesser amplitude could be used if the minimum value were increased, but this reduces the sensitivity.

The negative threshold wave $-T$ can be derived in numerous ways other than that shown, e.g., the output of the filter 4 could be applied to a peak detector and a DC voltage could be added to it. It is also apparent that a full wave rectifier could be used in place of the halfwave rectifier associated with the amplifier $A_1$, in which event its gain could be halved. In fact, the gain can be introduced at any point between the output of the high pass filter 4 and the inputs of the comparators $C_1$ and $C_2$ to which the threshold waves are applied.

The following values of impedance components and the following active devices have been found to give excellent results:

| R6 | 1K | R24 | 464K | $A_1$ | |
|----|----|-----|------|-------|---|
| R10 | 11K | R26 | 10K | $A_2$ | LF412 type |
| R12 | 4.22K | R28 | 10K | $A_3$ | op. amp. |
| R14 | 464K | R30 | 1K | $C_1$ | |
| R16 | 464K | R32 | 1 MEG | | LM393 type |
| C18 | 0.1 uf | R34 | 1 MEG | $C_2$ | comparator |
| R20 | 10K | R36 | 10K | | |
| R22 | 237 ohm | R38 | 100K | | |

The overall operation of the pace pulse detecting apparatus is as follows. Assume that the signal from the EKG machine 2 contains pace pulses such as $P_2$ and $P_3$ of FIG. 1A as well as QRS complexes such as $QRS_1$, $QRS_2$ and $QRS_3$. The high pass filter 4 eliminates the slow baseline drift, the muscle and movement artifacts M and the QRS complexes as indicated in FIG. 1B, but the pace pulses, noise spikes and high frequency noise HF remain. As seen in FIG. 1B, the positive threshold wave $+T$ is above the positive peaks of the high frequency noise HF. This is because of the amplification in the amplifier $A_1$ that is equal to or greater than $\pi$ and because of the fixed DC level provided by the voltage divider 20, 22. Thus, even when the signals have zero value or little or no high frequency noise, as at the left side of FIG. 1B, the positive threshold wave $+T$ will have a given value, and the negative threshold wave $-T$ will have a like negative value.

When no pace pulses are present, the outputs of the comparators $C_1$ and $C_2$ are in a high state. If a positive pace pulse such as $P_2$ or $P_3$ appears, the output of $C_1$ drops to a low state for the duration of the pace pulse; and if a negative pace pulse such as $P_4$ or $P_5$ appears, the output of $C_2$ drops to a low state for the duration of the pace pulse. The pulses produced by these changes in state are sufficient for identification purposes, but because we desire the output of the circuit to be well defined, the outputs of $C_1$ and $C_2$ are connected to the anode of a diode $d_1$, its cathode is connected to ground via a resistor 38 and the cathode of $d_1$ is connected to the input of a one-shot multivibrator 40 that is triggered by negative edges. When the outputs of $C_1$ and $C_2$ are high, $d_1$ conducts and the input of the multivibrator 40 is high, but the presence of a pace pulse causes the output of one of $C_1$ and $C_2$ to go low, so as to turn off $d_1$ and cause the input of the one-shot multivibrator 40 to drop to ground and fire the multivibrator 40. A high amplitude pulse of noise such as $N_2$ will cause the output of the comparator $C_1$ to drop to a low state, unfortunately firing the one-shot multivibrator 40, but such noise spikes do not occur often, and these false indications can be handled by the algorithms.

If it were not for the minimum value of the threshold waves provided by the voltage divider 20,22, any amount of noise, no matter how small, would cause one of the comparators $C_1$ and $C_2$ to change to a low state and thus falsely identify the noise as a pace pulse.

If the pace pulse identification circuit is to identify pace pulses of one polarity, only one threshold wave of that polarity and one of the comparators $C_1$ and $C_2$ are required.

In the embodiment of the invention shown in FIG. 1, the negative threshold wave $-T$ was derived first and the positive threshold wave $+T$ was derived by inverting $-T$, but the positive threshold wave $+T$ could be derived first and the negative threshold wave could be derived by inversion.

What is claimed is:

1. Apparatus for detecting the occurrence of a pace pulse included in signals having QRS complexes and which may also have muscle artifacts and steady noise, comprising
   filter means for suppressing frequency components of the QRS complexes, muscle artifacts and movement artifacts and passing frequency components higher than the frequencies of muscle artifacts,
   means coupled to said filter for deriving a threshold wave having a minimum amplitude when steady noise is absent and an amplitude equal to the sum of the minimum amplitude and the envelope of the peaks of steady noise when such noise is present, the said latter means acting to suppress the effects of pace pulses on the amplitude of the threshold wave, and
   comparing means coupled to said filter and to said means for deriving a threshold wave for providing a pace pulse detection signal whenever the amplitude of the signals passing through said filter exceeds the amplitude of the threshold wave.

2. Apparatus as set forth in claim 1 having
   means for producing another threshold wave having a polarity that is opposite to that of the first threshold wave, and
   means coupled to the output of said filter and to said means for deriving another threshold wave for providing a pace pulse identification signal whenever the amplitude of the signals passing through said filter exceeds the amplitude of said another threshold wave.

3. Apparatus as set forth in claim 1 wherein said filter has means for suppressing below 1000 c.p.s.

4. A circuit capable of indicating the presence of a pace pulse in signals that may have any combination of QRS complexes, muscle artifacts, movement artifacts, steady high frequency noise and baseline wander, comprising:
   a high pass filter that passes high frequency noise and at least some of the high frequency components of a pace pulse to its output and which supresses QRS complexes, muscle artifacts, movement artifacts or baseline wander
   a comparator having a first input coupled to the output of said high pass filter,
   rectifying means coupled to the output of said high pass filter,
   integrating means for deriving a threshold voltage coupled to the output of said rectifying means, the time constant of said integrating means being such that its output voltage is an average value of any steady high frequency noise present at the output of said rectifying means and unaffected by pace pulses, and
   means for coupling the output of said integrating means to a second input of said comparator, whereby the presence of a pace pulse causes said comparator to change state.

5. A circuit as set forth in claim 4 wherein means are provided for making the value of said threshold voltage at least equal to the amplitude of steady high frequency noise at said first input of said comparator.

6. A circuit as set forth in claim 5 wherein means are provided for adding a predetermined DC voltage to the threshold voltage.

7. A circuit as set forth in claim 4 wherein means are provided for making said threshold voltage at least $\pi$ times the average value of any steady high frequency noise at the output of said high pass filter.

8. A circuit as set forth in claim 4 wherein means are provided for making the ratio of the threshold voltage to the average value of steady high frequency noise that is coupled to the first input of said comparator at least equal to 3.6.

9. A circuit capable of indicating the presence of a pace pulse in signals that may have any combination of QRS complexes, muscles artifacts, movement artifacts, steady state high frequency noise and baseline wander, comprising
   filter means having an input to which such signals may be applied and an output at which only at least some of the high frequency components of pace pulses and noise having a frequency that is higher than the frequencies contained in QRS complexes, muscle artifacts, movement artifacts and baseline wander appear,
   a comparator having first and second inputs,
   means for coupling the output of said filter means to said first input of said comparator,
   means coupled to the output of said filter means for providing a threshold voltage at said second input of said comparator that has the same polarity as pace pulses applied to the first input of said comparator, said latter means having a time constant such that pace pulses have a negligible effect on the amplitude of the threshold voltage, and
   means for causing the relative amplitude of steady state noise applied to said first input of said comparator and the threshold voltage applied to the second input of said comparator to be such that the threshold voltage is at least as great as the peaks of the steady state noise.

10. A circuit capable of indicating the presence of a pace pulse in signals that may have any combination of QRS complexes, muscle artifacts, movement artifacts, steady state high frequency noise and baseline wander, comprising filter means having an input to which such signals may be applied and an output at which only at least some of the frequency components of pace pulses and high noise having a frequency that is higher than the frequencies contained in QRS complexes, muscle artifacts, movement artifacts and baseline wander appear, a comparator having first and second inputs, means for coupling the output of said filter means to said first input of said comparator, means coupled to the output of said filter means for providing a threshold voltage at said second input of said comparator having a value equal to the sum of a fixed value and a value proportional to the average value of signals at the output of the filter means that are on one side of the baseline, and means for causing the relative amplitude of steady state noise applied to said first input of said comparator and the threshold voltage applied to the second input of said comparator to be such that the threshold voltage is at least as great as the peaks of the steady state noise.

* * * * *